(12) United States Patent
Gensler

(10) Patent No.: US 7,229,546 B1
(45) Date of Patent: Jun. 12, 2007

(54) METHOD AND APPARATUS FOR MEASURING SUCROSE TRANSPORT INTO THE FRUIT OF PLANTS

(76) Inventor: William George Gensler, 4020 E. Coronado Dr., Tucson, AZ (US) 85718

( * ) Notice: Subject to any disclaimer, the term of this patent is extended or adjusted under 35 U.S.C. 154(b) by 0 days.

(21) Appl. No.: 11/260,741

(22) Filed: Oct. 27, 2005

Related U.S. Application Data

(60) Provisional application No. 60/622,990, filed on Oct. 29, 2004.

(51) Int. Cl.
*G01N 27/327* (2006.01)
*G01N 27/403* (2006.01)

(52) U.S. Cl. .................. 205/792; 205/787
(58) Field of Classification Search .......... 205/775, 205/777.5, 792, 787; 204/403.01, 400; 47/1.01 R
See application file for complete search history.

(56) References Cited

U.S. PATENT DOCUMENTS

| 3,967,198 A | 6/1976 | Gensler |
| 6,870,376 B1 | 3/2005 | Gensler |

FOREIGN PATENT DOCUMENTS

JP  08-247994 A  *  9/1996

OTHER PUBLICATIONS

The Derwent abstract and the figure of Chernitski et al. (SU 1606015 A) published Nov. 15, 1990.*
JPO English language translation of Yoshinori et al. (08-247994 A) published Sep. 27, 1996.*
Chakkaravarthy ("Plant bioelectropotential and its origin," Bulletin of Electrochemistry (1987), 3(2), 191-4).*

* cited by examiner

*Primary Examiner*—Alex Noguerola

(57) ABSTRACT

The method and apparatus are concerned with measurement of the onset and magnitude of sucrose transport between a petiole and fruit within a plant over extended time periods. Sensors are implanted in both the petiole and fruit. The electrical potential of each sensor is measured with respect to a common electrode in the soil. A difference potential is formed by subtracting the potential of the sensor in the fruit from the potential of the sensor in the petiole. Positive values of this difference determine the onset and magnitude of sucrose transport between the petiole and fruit. Cumulative values of positive difference potential over a multi-day period yield the contribution of the leaf and petiole to sugar buildup in the fruit. The cumulative positive difference potential is specific to the location of the sensors. This has the advantage that multiple sensors in petioles in the same stem yield a continuous measure of sucrose allocation, or non allocation, from the different petioles to the fruit.

4 Claims, 3 Drawing Sheets

METHOD AND APPARATUS FOR MEASURING SUCROSE TRANSPORT INTO THE FRUIT OF PLANTS

Figure 1:
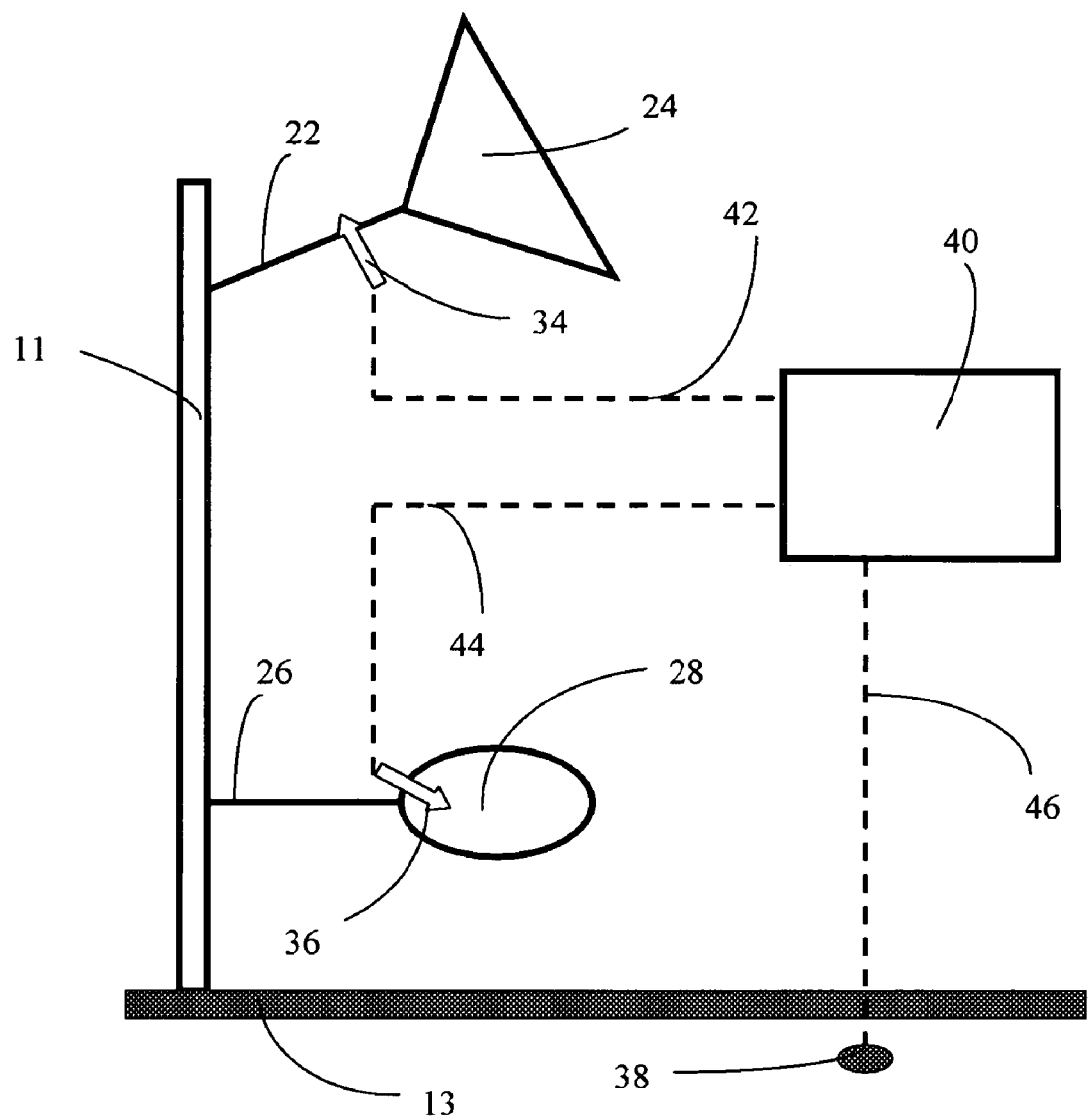

This application claims priority from U.S. Provisional Application No. 60/622,990, filed Oct. 29, 2004.

BACKGROUND REFERENCES

U.S. Pat. No. 3,967,198 William G. Gensler. Jun. 29, 1976. Method and Apparatus for Electrically Determining Plant Water Status U.S. Pat. No. 6,870,376 B1 William G. Gensler. Mar. 22, 2005. Method and Apparatus for Determining Plant Water Content U.S. Provisional Patent Application 60/622,990. William G. Gensler, Method and Apparatus for Measuring Sucrose Transport into the Fruit of Plants Gensler, W. Measuring and interpreting diurnal activity in the main stem of tees. Chapter in Tree Ring Analysis, Biological, Methodological and Environmental Aspects. R Wimmer and R. E. Vetter, Editors, CABI Publishing, Wallingford, Oxon, UK, 1999.

Hale, C. R. and R. J. Weaver. The effect of developmental stage on direction of translocation of photosynthate in *Vitis vinifera*. Hilgardia (Berkeley, Calif.) 33:89-131, 1962.

Hoare, J. Oxygen. Chapter in Standard potentials in aqueous solutions. A. J. Bard, R. Parsons and J. Jordan, Editors, Marcel Dekker, Inc. New York, 1985.

Kliewer, W. M. Changes in concentration of glucose, fructose and total soluble solids in flowers and berries of *Vitis vinifera*. American Journal of Enology and Viticulture 16: 101-110, 1965.

Nobel, P. S. Physicochemical and Environmental Plant Physiology. Academic Press, 1991.

Pirson, A. and M. H. Zimmermann, Editors. Phloem Transport, Encyclopedia of Plant Physiology, New Series, Volume 1. Springer-Verlag, Berlin, 1975.

Rugenstein, S. Tissue Response to palladium microprobe as observed in *Gossypium hirsutum*, L (Malvaeceae). American Journal of Botany, 64: 519-528, 1982.

Seymour, G. B., J. E. Taylor and G. A. Tucker. Biochemistry of Fruit Ripening. Chapman and Hall, London, 1993.

Taiz, L. and E. Zeigler, Plant Physiology. Sinauer Associates, Inc., Sunderland, Mass. 2002.

Vracar, I. M., D. B. Sepa and A. Aamjanovic. Palladium electrode in oxygen saturated solutions. Journal of the Electrochemical Society, 134:1695-1697, 1987.

Zeigler, H. Nature of Transported Substances. Chapter in Encyclopedia of Plant Physiology, New Series, Volume 1. Phloem Transport. A. Pirson and M. H. Zimmermann, Editors. Springer-Verlag, Berlin, 1975.

FIELD OF INVENTION

This invention relates to a method and apparatus to measure sucrose transport into the fruit of plants

DISCUSSION OF PRIOR ART

At the present time there is no non-destructive method of determining the timing and magnitude of sucrose transport into the fruit of plants. The most common method of determining the amount of sugar that has accumulated in the fruit is to excise the fruit, squeeze the juice out of the fruit and measure the sugar accumulation with a refractometer. The assumption is made that the dominant soluble solid component of the juice is sugar and the reading of the refractometer gives the quantity of sugar present in terms of a ratio of amount of sugar to the total amount of sugar plus water present in the sample. This method is effective but has the disadvantages of removing the fruit from the plant, destruction of the sample, high labor content and the need for numerous sequential readings to obtain the trend in sugar accumulation.

My apparatus and method does not have these disadvantages. A continuous, non-destructive, automatic measurement may be made and the information transferred manually at the site or remotely by telemetry at minimal labor content. The apparatus for the measurement of sucrose transport into the fruit requires a sensor in the petiole and a sensor in the fruit. The method requires a measurement of electrical potential between the sensor in the petiole of the leaf and the sensor in the fruit and a computation of the difference between the two measured potential values.

There are two distinct differences in the method and apparatus of U.S. Pat. No. 3,967,198 and the method and apparatus of this invention. The use of the method and apparatus in U.S. Pat. No. 3,967,198 is for measurement of plant water status. The use of the present invention is for measurement of sucrose transport into the fruit of plants. These are completely different uses. The method in U.S. Pat. No. 3,967,198 does not require, nor makes no mention, of a computation of the difference in the potential of two sensors. The method in the present invention requires this computation for a determination of sucrose transport.

There are several distinct differences in the method and apparatus of U.S. Pat. No. 6,870,376 B1 and the method and apparatus of this invention. The use of the method and apparatus in U.S. Pat. No. 6,870,376 B1 is for measurement of plant water status. The use of the present invention is for measurement of sucrose transport into the fruit of plants. These are completely different uses. The apparatus for the measurement of plant water content in U.S. Pat. No. 6,870,376 B1 requires a sensor in the petiole alone and a common electrode in the root environment. There are two measurements. The first measurement is the electrical capacitance of the sensor in the plant. The second measurement is the area of the sensor surface within the plant. The capacitance and area measurements are combined to yield a ratio. This ratio is then used for determination of plant water content. The apparatus and method in this invention requires sensors in two locations within the plant and a common electrode in the root environment. A single measurement, electrical potential, is made on each sensor in the plant. The potential of the sensor in the second location is then subtracted from the potential in the first location to yield a difference potential. This difference potential is then used to determine sucrose transport.

The common electrode is the same in the method and apparatus of U.S. Pat. No. 6,870,376, U.S. Pat. No. 3,967,198 and the present invention.

Prior Art: Plant Physiology

Plants produce sugar in the leaves. At the whole plant level, this sugar is transported to the roots, the growing tip of the shoot and the fruit (Taiz and Zeigler). The sugar is primarily transported as sucrose (Taiz and Zeigler, Zeigler, H.) Sucrose is a neutral molecule with a molecular weight of 342 grams. At the cellular level, sucrose is transported from outside the cells to inside the cells. This transfer is accomplished by first attaching the large and heavy sucrose molecule present outside the cell to a hydrogen ion, (referred to as a proton) to produce a combination termed "charged sucrose." The cell membrane itself is electrically charged with the outside surface of the membrane more positive than the inside surface of the membrane. The sucrose/proton combination moves across the cell membrane aided by this electrical potential gradient.

The proton in this mechanism is an "uncompensated" proton. This is a proton that has no counter ion in the vicinity. The negatively charged counter ion is inside the cell. This separation is a result of an electrogenic process whereby protons are forced through the cell membrane leaving the negative ion behind (Taiz and Ziegler, Nobel). The cells in plants maintain an extracellular region which has electrical potential derived from this aggregation of uncompensated protons.

Prior Art: Electrochemistry

A noble metal surface immersed in water exchanges electrons with the oxygen absorbed on the surface (Hoare). The oxygen constantly ionizes and deionizes. These reactions involve protons. This results in an interfacial potential sensitive to proton concentration. Quantitatively, the proton sensitivity is 60 millivolts per log unit change in proton concentration (Vracar, Gensler). This variation is measured by the sensor in the immersed in the fluid in the plant tissue to electrically determine changes in proton concentration.

OBJECTS AND ADVANTAGES

The apparatus and method described herein is built upon the plant physiology and electrochemistry of prior art and field applications in agriculture and forestry. The result is a quantitative measurement of sucrose transport between petiole and fruit. This measurement is made non-destructively, continuously and automatically. When the measurement is made over a period of time, the result gives the onset and magnitude of sucrose transport between the petiole and fruit. A cumulative measure of sucrose transport can be obtained by adding up the daily contributions to transport. In this manner, the contribution, or non-contribution, to sucrose buildup in the fruit from the leaf associated with the petiole can be obtained. Fruit ripening can be quantified.

Since allocation of sucrose from different leaves to different regions of the plant as a whole varies during the life of the plant, the onset and magnitude of sucrose transport from a given petiole within a plant gives insight into the contribution of other leaves apical or basal to the leaf whose petiole is monitored. For example, leaves near the shoot tip may direct sucrose to the shoot tip as opposed to the fruit until the final stages of the season (Hale and Weaver). Multiple sensors implanted in different petioles along the same stem can give an indication of the direction and magnitude of sucrose transport from the different petioles in different parts of the stem. In this way, whole plant allocation of sucrose can be quantified.

DRAWINGS

FIG. 1 gives a description of the sensors in the petiole and fruit, the wires which connect the sensors to the voltmeter, and the wire to the common electrode.

Figure 2:
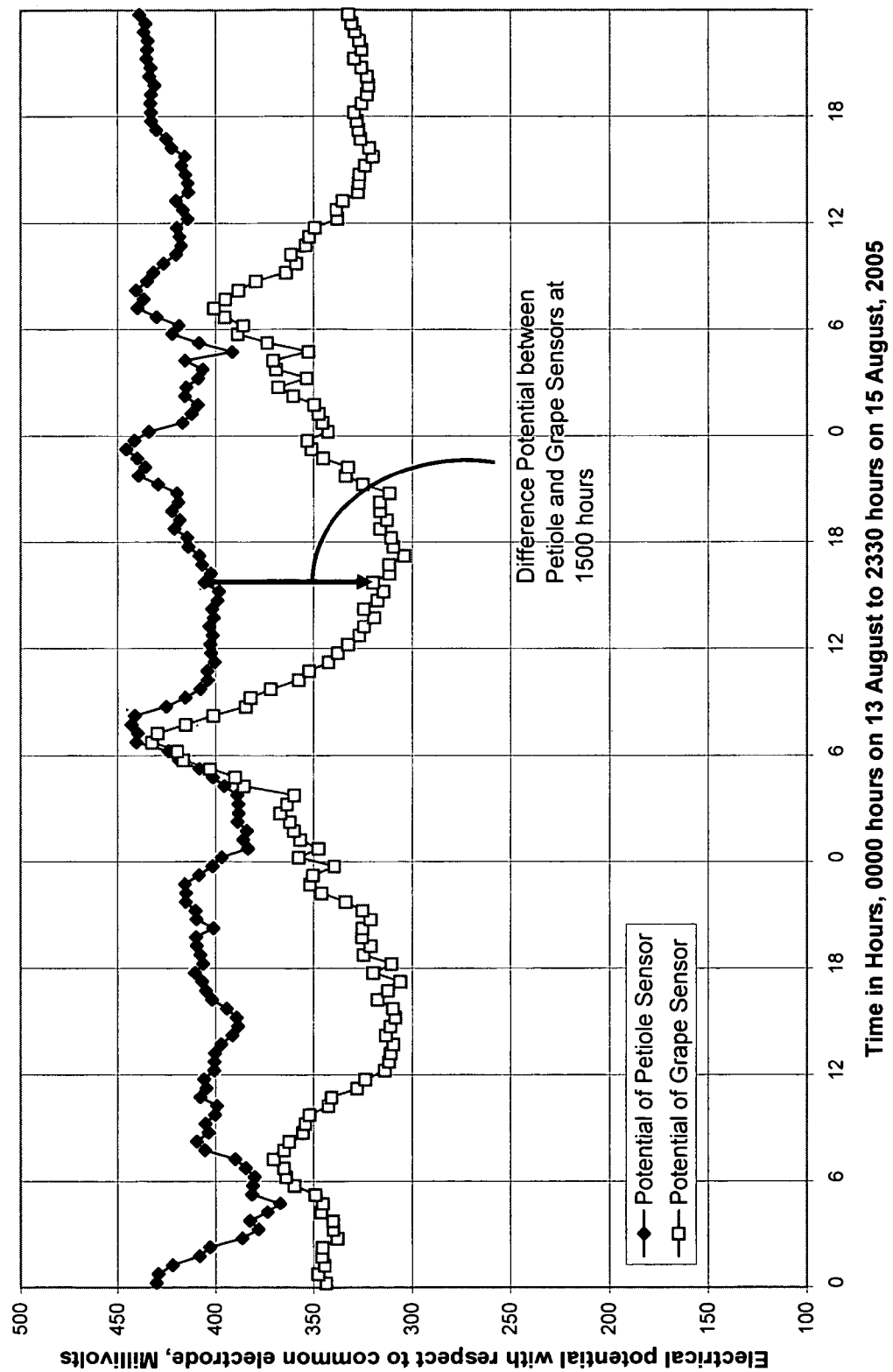

FIG. 2 gives an example of the potential values of the petiole and grape in a cabernet sauvignon wine grape vine over a three day period. The difference potential is positive most of the time. This indicates an almost continuous movement of sucrose from the petiole to the fruit during each twenty-four hour diurnal cycle. This is the situation observed in plants growing in warmer climates.

Figure 3:
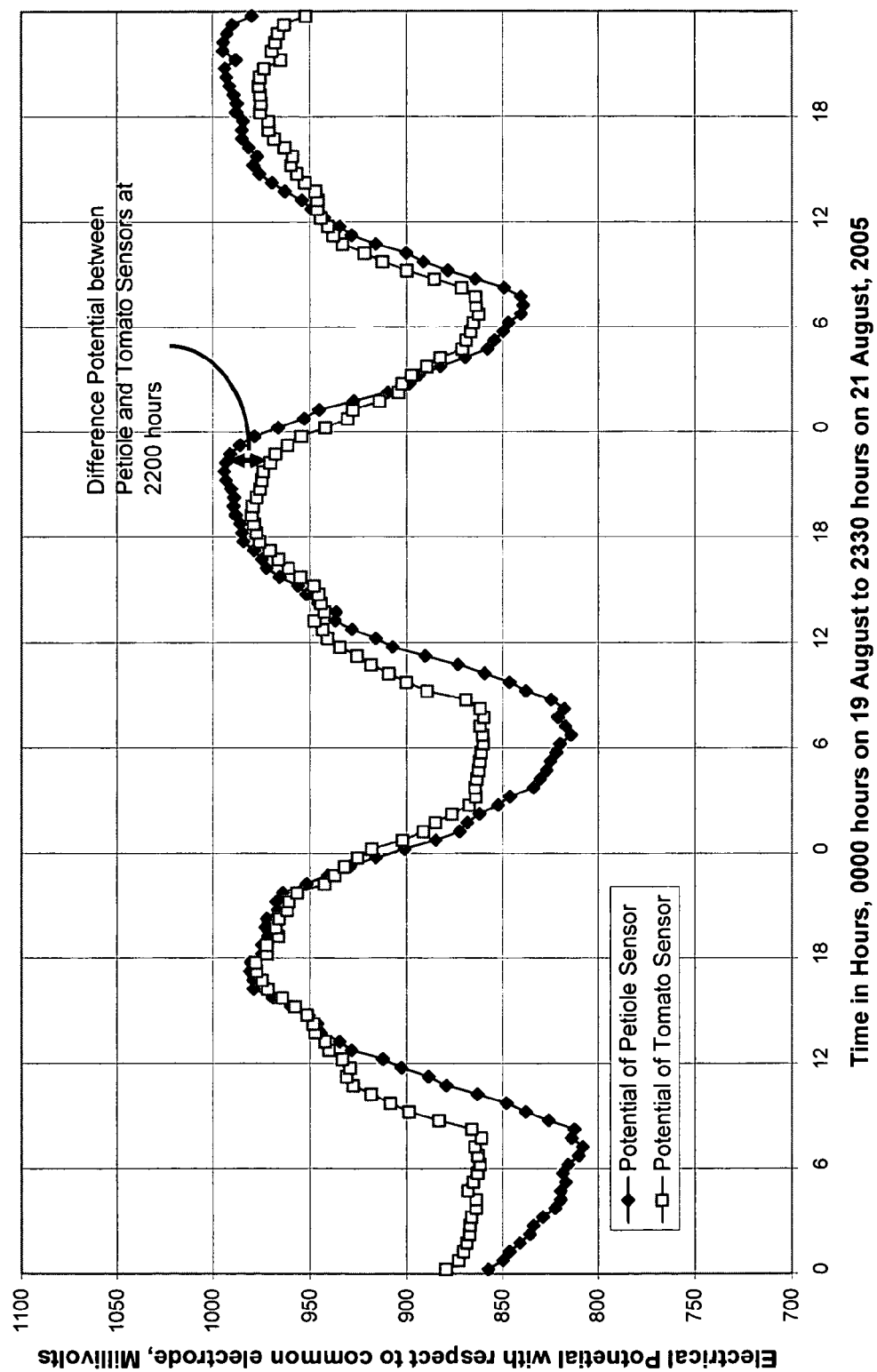

FIG. 3 gives an example of the potential values of the petiole and tomato in a processing tomato vine over a three day period. The difference potential is positive for only a limited time, mainly in the late afternoon. This indicates slow buildup of sugar. Tomato fruit has a low level of sugar buildup even in warmer climates.

LIST OF NUMERALS

11 Plant stem
13 Surface of the soil
22 Petiole of the Leaf (The petiole is the stem of the leaf)
24 Leaf
26 Peduncle of the Fruit (The peduncle is the stem of the fruit)
28 Fruit
34 Sensor in the Petiole
36 Sensor in the Fruit
38 Common Electrode
40 Voltmeter
42 Wire from Petiole Sensor to the Voltmeter
44 Wire from Fruit Sensor to the Voltmeter
46 Wire from the common electrode to the Voltmeter To enhance clarity, the wires from the sensors and the common electrode to the voltmeter are dashed lines.

SUMMARY

Sensors are implanted in a petiole and fruit. The electrical potential of each of these sensors is measured with respect to a common electrode. A difference potential is calculated by subtracting the potential of the fruit from the potential of the petiole. Positive values of difference potential yield a numerical value proportional to the rate of sugar transport between the two parts of the plant containing the sensors. The sequence of values taken during successive time periods is added to produce a daily cumulative difference potential. This procedure is then extended for multi-day time intervals to produce a multi-day cumulative difference potential. This multi-day cumulative difference potential yields a value proportional to the total magnitude of sugar transported between these two parts of the plant.

DESCRIPTION OF INVENTION

Theory of Sucrose Movement from Source to Sink

There is no widely accepted theory of sucrose movement from leaf to fruit (Pirson and Zimmerman). The pressure-flow model of Munch is widely accepted but still controversial (Taiz and Zeigler). The premise which I make herein is that the short distance lateral movement of charged sucrose from the cells to the phloem is a result of a lateral electrical potential gradient. Further, electrical potential continuity exists within the phloem. When the sucrose emerges from the phloem, it once again moves as charged sucrose to the extracellular region of the absorbing cells in the fruit under an electrical potential gradient. Overall, there is electrical continuity between the source in the petiole and the sink in the fruit.

Mechanism of Transport

A higher concentration of sucrose is concomitant with a higher concentration of protons. An aggregation of electrical charge of one polarity results in an electrical potential in the location of the aggregation relative to a region that does not contain charge. The sensor placed in the region gives a measure of this potential. Sensors placed in two regions give a measure of the relative difference in the proton concentration of the two regions and, in turn, the relative difference in the sucrose concentration of the two regions. This is the case with sensors placed in the extracellular regions of the petiole and fruit. This relative difference then induces sucrose movement between the petiole and the fruit. The force-flow relation can be expressed as follows:

Electrical Potential Difference between Two Regions=Resistance in the Pathway between the Two Regions*Rate of Sucrose Transport In electrical variables:

$$\Delta V = R*I$$

where V is in units of volts, R is in units of ohms and I is in units of coulombs per second.

The $\Delta V$ is obtained from subtracting the potential of the sensor in the fruit from the potential of the sensor in the petiole. A positive difference potential is indicative of a movement of sucrose from source in the leaf to sink in the fruit. A negative difference potential is indicative a lack of movement from source to sink since the fruit does not feed sucrose to the leaf.

The variable $\Delta V$ gives a measure of the rate of sucrose transport time proportionality constant. The proportionality constant is determined by the resistance in the pathway between the two regions.

Detailed Description of the Apparatus

The apparatus is described in FIG. 1. Petiole 22 and subtended leaf 24 are attached to plant stem 11. Peduncle 26 and subtended fruit 28 are also attached to stem 11. Sensor 34 is implanted through petiole 22. Sensor 36 is implanted in fruit 28. Wire 42 connects sensor 34 to voltmeter 40. Wire 44 connects sensor 36 to voltmeter 40. Wire 46 connects the common electrode 38 to voltmeter 40. The common electrode is located beneath the soil surface 13.

Since the variable of importance is a difference potential, any variation in interfacial potential between the common electrode and the soil is not relevant. This same conclusion holds true for any changes in potential along the shared path between the common electrode 38 and the sensors 34 and 36.

The sensor 34 in the petiole 22 is placed near the junction of the petiole 22 with the stem 11. This minimizes the influence of wind induced movement of wire 34 and sensor 34. Sensor 34 is implanted diametrically through and out the other side of petiole 22. Sensor 36 is implanted in the upper shoulder of the fruit 28 near the junction of peduncle 26 with fruit 28. This insures integrity of the skin of fruit 28.

Sensors 34 and 36 are implanted at the upper shoulder of the "S" curve of growth (Rugenstein). This is the period when the tissue is past juvenility and in the middle of the maturity phase of growth. In a sequence of petioles and leaves along a stem, implant would be in the petiole of the top fully developed leaf. This minimizes scar tissue formation at the surface of the sensor inside the plant. This insures integrity to the measurement over an extended period.

For determination of sucrose transport of multiple leaves over an extended period, multiple sensors in multiple petioles could be implanted in the manner shown in FIG. 1. Multiple sensors in multiple fruit could be implanted in a similar manner for the same determination.

The voltmeter is selected which requires minimum energy drain on the sensor during the measurement. This insures integrity of the measured potential. The plant is not enervated by the measurement. Continual measurements are possible. This is a major advantage of the apparatus.

OPERATION OF INVENTION

The operation of the invention takes place in three sequential steps (refer to FIG. 1):

a: Installation of Components

Sensor 34 is implanted in petiole 22. Sensor 36 is implanted in fruit 28. The common electrode 38 is buried in the ground.

A wire 42 is connected between sensor 34 and voltmeter 40. A wire 44 is connected between sensor 36 and voltmeter 40. A wire 46 is connected between common point 38 and voltmeter 40.

b: Measurement of Potentials

The potential of sensor 34 with respect to common electrode 38 is measured by voltmeter 40.

The potential of sensor 36 with respect to common electrode 38 is measured by voltmeter 40.

c: Computation of Difference Potential

The potential of sensor 36 with respect to common electrode 38 is subtracted from the potential of sensor 34 with respect to common electrode 38 to yield a difference potential.

The magnitude of positive difference potential is proportional to the magnitude of sucrose transport from petiole 22 to fruit 28.

CONCLUSIONS, RAMIFICATIONS AND SCOPE OF INVENTION

Conclusions

This invention is an apparatus comprised of sensors which are invasive, non-destructive and can be resident in the plant for extended time periods. This invention is also a method which derives from this apparatus a numerical value which is proportional to the rate of sugar transport between the two parts of the plant containing the sensors.

The apparatus and method will measure a difference potential which is proportional to the rate of movement of sucrose from a source in the plant to a sink in the plant. The source is not limited to the petiole but can be any source of sucrose generated within the plant. The sink is not limited to the fruit but can be any part of the plant that adsorbs, or transmits, sucrose.

A sequence of difference potential derived from a sequence of potential measurements can be accumulated to yield a cumulative difference potential over a multi-day period. The net cumulative difference potential over a single day is subject to the vagaries of the weather and condition of the plant on that particular day. A cumulative difference potential over multiple days smoothes the variability from day to day and gives an overall understanding of the long term process of fruit ripening.

RAMIFICATIONS

Placement in the leaf blade is an alternate to placement in the petiole, but the latter is more desirable because of its relative insensitivity to external influences such as wind loading. Placement in the fruit must be made at a location which does not compromise the integrity of the skin of the fruit. Such a location is the upper shoulder of the fruit in the vicinity of the sepals.

An alternate to placement in the fruit itself may be placement in the direct path to the fruit. This could be, for example, placement in the peduncle (the stem leading into the fruit) of the fruit. This latter placement has the advantage of measuring the sucrose transport to several fruit in a cluster. For example, this is the situation with wine grapes and tomatoes.

The size of the sensor should be as small as possible to insure minimum impact on the normal functioning of the tissue contiguous to the sensor surface for the duration of residence of the sensor in the tissue. A preferred embodiment of the physical shape of the sensor is a filament, that is, a shape that is long, needle-like and resists deformation.

The time of implant within the life cycle of the plant is important because implant in overly juvenile tissue will induce scar tissue formation in the vicinity of the sensor.

The shape of the sensor is not significant. A filament has two advantages. The first advantage of a filament is the minimum tendency to deform during implant. The second advantage of the circular shape is the minimum disturbance it has on fluid movement in the vicinity of the sensor. The cells in the vicinity of the filament can function in a near-normal manner.

The material which the sensor is made of must be compatible with the chemical environment within the plant. It cannot cause necrosis of the tissue in its vicinity. The material which the sensor is made of also is significant insofar as chemical reactions at the surface must include protons to yield a change of interfacial potential to proton concentration changes in the fluid surrounding the surface. The material is also important insofar any other exchange of electrons from the material of the sensor with reactants in the fluid have negligible influence on changes in the interfacial potential.

The difference potential which accrues from the measurement of the potentials of the petiole and fruit are specific to the petiole containing the sensor and the fruit containing the sensor. The onset and magnitude of sucrose transport are specific to these locations. This specificity has the advantage of delineating sucrose transport between definite parts of the plant and reveal the contribution or non-contribution of the specific petiole to sucrose buildup. Additional sensors implanted in other petioles and additional measurements of their potentials can then reveal the relative contribution to fruit ripening of different parts of the same plant. The timing and magnitude of sucrose transport has strong influence on flavor. This is manifest in the desirability of "vine-ripened" fruit (Seymour, et al).

The computation of a difference potential renders the resulting value insensitive to variations in the interfacial potential of the common electrode with the soil. A flush of irrigation water through the soil and the resultant change in interfacial potential at the common electrode/soil interface has no influence on the value. In like manner, any change in potential in the common pathway to the two sensors from the common electrode has no influence on the difference potential.

SCOPE OF INVENTION

Although the above description contains many specificities these should not be construed as limitations on the scope of the invention, but rather as exemplifications of one preferred embodiment thereof.

Accordingly, the scope of the invention should be determined not by the embodiment but by the appended claims and their legal equivalents.

I claim:

1. A method for measuring sucrose transport between part one and part two within a plant comprising the steps of:
   placing sensor one in said part one within said plant,
   placing sensor two in said part two within said plant
   placing a common electrode in the root environment,
   measuring electrical potential one between a first wire connected to said sensor one and a third wire connected to said common electrode in said root environment,
   measuring electrical potential two between a second wire connected to said sensor two and said third wire connected to said common electrode in said root environment,
   calculating difference one formed by subtracting said electrical potential two from said electrical potential one, and
   forming positive values of difference one to determine said sucrose transport between said part one and said part two within said plant.

2. Apparatus for measuring sucrose transport between part one and part two within a plant comprised of
   sensor one means for implanting in said part one of said plant,
   sensor two means for implanting in said part two of said plant,
   common electrode for making contact with the root environment,
   first wire connected to said sensor one means, second wire connected to said sensor two means, third wire connected to said common electrode,
   means coupled to said first wire and said third wire for measuring electrical potential one generated therebetween by said plant
   means coupled to said second wire and said third wire for measuring electrical potential two generated therebetween by said plant
   means for calculating difference one by subtracting said electrical potential two from said electrical potential one, and
   means to determine said sucrose transport when value of said difference one is positive.

3. Apparatus as recited in claim 2 further including a plurality of sensor means and means interposed between each of said sensors and said measuring means for selectively connecting each one of said sensor means to said measuring means.

4. Apparatus as recited in claim 3 further including a means to compute the plurality of said difference potentials which accrue from the said plurality of said sensor means.

* * * * *